United States Patent [19]

Shindler et al.

[11] Patent Number: 5,405,012
[45] Date of Patent: Apr. 11, 1995

[54] INSULATED CONTAINER FOR TRANSPORTING TEMPERATURE SENSITIVE ANALYTICAL SAMPLES

[75] Inventors: Steven J. Shindler; Akihiko Seki, both of New York, N.Y.

[73] Assignee: Purisys Inc., New York, N.Y.

[21] Appl. No.: 135,885

[22] Filed: Oct. 13, 1993

[51] Int. Cl.⁶ .............................................. B65D 81/18
[52] U.S. Cl. ................................... 206/569; 62/457.1; 206/523; 220/412
[58] Field of Search .................... 62/372, 457.1, 457.7, 62/457.9; 126/261, 263 R; 206/523, 545, 569, 570; 220/23.83, 412, 413, 501

[56] References Cited

U.S. PATENT DOCUMENTS

| | | | |
|---|---|---|---|
| 2,496,296 | 2/1950 | Lobl | 206/545 |
| 2,555,126 | 5/1951 | Greve | 206/545 |
| 3,251,460 | 5/1966 | Edmonds | 206/523 |
| 3,670,918 | 6/1972 | Mitchel | 206/545 |
| 4,106,597 | 8/1978 | Shook et al. | 206/545 |
| 4,119,248 | 10/1978 | Butler et al. | 220/412 |
| 4,240,547 | 12/1980 | Taylor | 206/204 |
| 4,286,440 | 9/1981 | Taylor | 206/541 |
| 4,368,819 | 1/1983 | Durham | 220/412 |
| 4,826,003 | 5/1989 | Levy | 206/45.31 |
| 4,911,300 | 3/1990 | Colonna | 206/433 |
| 5,040,678 | 8/1991 | Lenmark, Sr. et al. | 62/457.7 |

FOREIGN PATENT DOCUMENTS 2127783 4/1984 United Kingdom ................ 206/541

*Primary Examiner*—Jimmy G. Foster
*Attorney, Agent, or Firm*—Brooks Haidt Haffner & Delahunty

[57] ABSTRACT

An insulated specimen shipping container is disclosed having a base and a cover fitting thereon. The base includes a compartment for receiving a cold pack and several sockets for receiving specimens. A portion of the interior wall separating the cold pack from the specimens has openings, facilitating thermal communication between the specimens and cold pack.

17 Claims, 4 Drawing Sheets

INSULATED CONTAINER FOR TRANSPORTING TEMPERATURE SENSITIVE ANALYTICAL SAMPLES

BACKGROUND OF THE INVENTION

1. Field of the Invention

The present invention relates to insulated containers and, more particularly to containers for transporting temperature sensitive analytical specimens.

2. Description of the Related Art

Biological and chemical specimens and other temperature sensitive materials are frequently shipped through the mail to distant locations, e.g. laboratories for testing and analysis. In order to preserve the specimens it is thus necessary to provide a secure shipping container which protects the enclosed specimens against rough handling and other shocks received during transport. U.S. Pat. No. 4,240,547, for instance, describes a two-piece, symmetrical package utilizing shock absorbent material to protect the enclosed specimens. Similarly, U.S. Pat. No. 4,826,003 describes a package made of a molded material and having pockets to hold the specimens therein.

Since certain biological and chemical specimens must be kept cool for analysis, these specimens also require thermal protection to preserve them during transport. U.S. Pat. No. 4,826,003 describes molding a container out of polystyrene or styrofoam, materials having good thermal insulation properties. The described container, however, includes several viewing slots through the outer walls for identifying the enclosed contents, preventing suitable insulation. Further, the described container does not include a cold pack or other device to regulate and maintain cool temperatures during transport.

Other insulated specimen containers are known which have a space to accommodate a cold pack in its unfrozen state and wherein the specimens are insulated from the cold pack. When the cold pack is frozen, however, it expands and does not fit in the space which accommodates it in its unfrozen state.

Although the aforesaid containers provide some protection during transport, there is a need for an improved container which not only protects the enclosed specimens from physical damage but also insulates them from thermal damage by maintaining the internal temperature within a specified range.

It is an object of the present invention to provide such an insulated container in which to ship biological, chemical or other specimens requiring both physical and thermal protection, whereby thermal communication between an enclosed cold pack and the specimens is facilitated by the thermal cooperation between channels, compartments and recesses in the insulated container.

SUMMARY OF THE INVENTION

In accordance with a preferred embodiment of the present invention, a specimen shipping container includes a base and a cover fitting thereon. The base includes a compartment for receiving a temperature regulating means, e.g., a cold pack, and also includes a plurality of sockets for receiving the specimens. A portion of the interior wall separating the temperature regulating means from the specimens has channels which facilitate thermal circulation between the specimens and temperature regulating means. Circulation is further improved by providing ribs along the interior surface of the sockets, facilitating circulation around the enclosed specimens.

BRIEF DESCRIPTION OF THE EMBODIMENTS

The invention will be better understood after reading the following detailed description of the preferred embodiments with reference to the appended drawings in which.

The same reference numbers are used throughout the drawings to designate the same or similar parts.

DETAILED DESCRIPTION OF THE PREFERRED EMBODIMENTS

Figure 1:
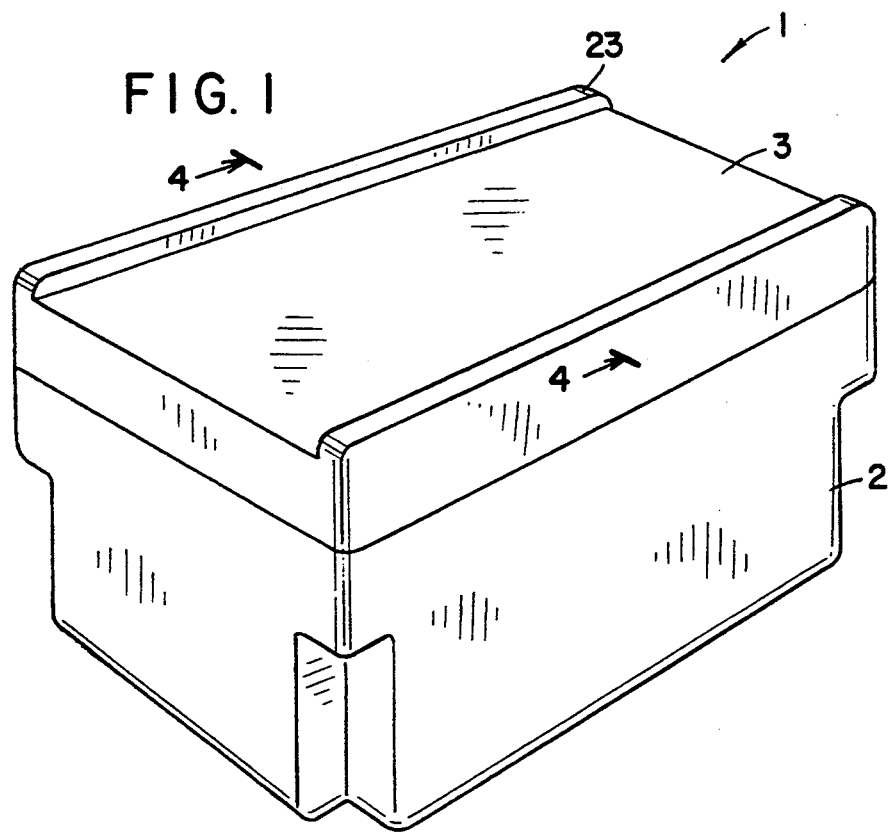
FIG. 1 is a front perspective view of the container of the present invention showing a base and its cover.

Referring now to the drawings, there is shown in FIG. 1 a preferred embodiment of a container 1 for transporting temperature sensitive materials, such as biological and chemical specimens, to a laboratory for testing and analysis.

Container 1 comprises a base 2 and cover 3, which overlies the base 2. Both the base 2 and cover 3 are preferably made of a light-weight material which can be easily molded, e.g., polystyrene, expanded polystyrene (EPS) or styrofoam plastic foam, which not only protects the contents from physical damage but also has good thermal insulation properties. Preferably, the material used in the base 2 and cover 3 is recycled and/or recyclable.

Figure 2:
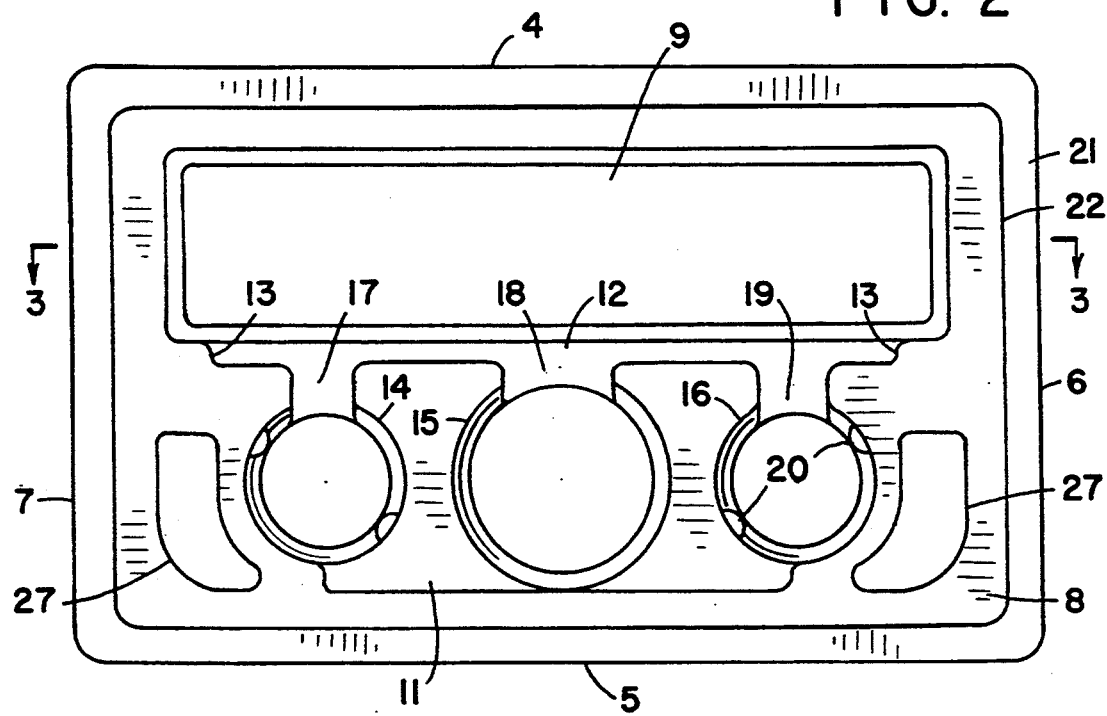
FIG. 2 is a top view of the base in FIG. 1 showing the empty rectangular compartment and sockets.
Figure 3:
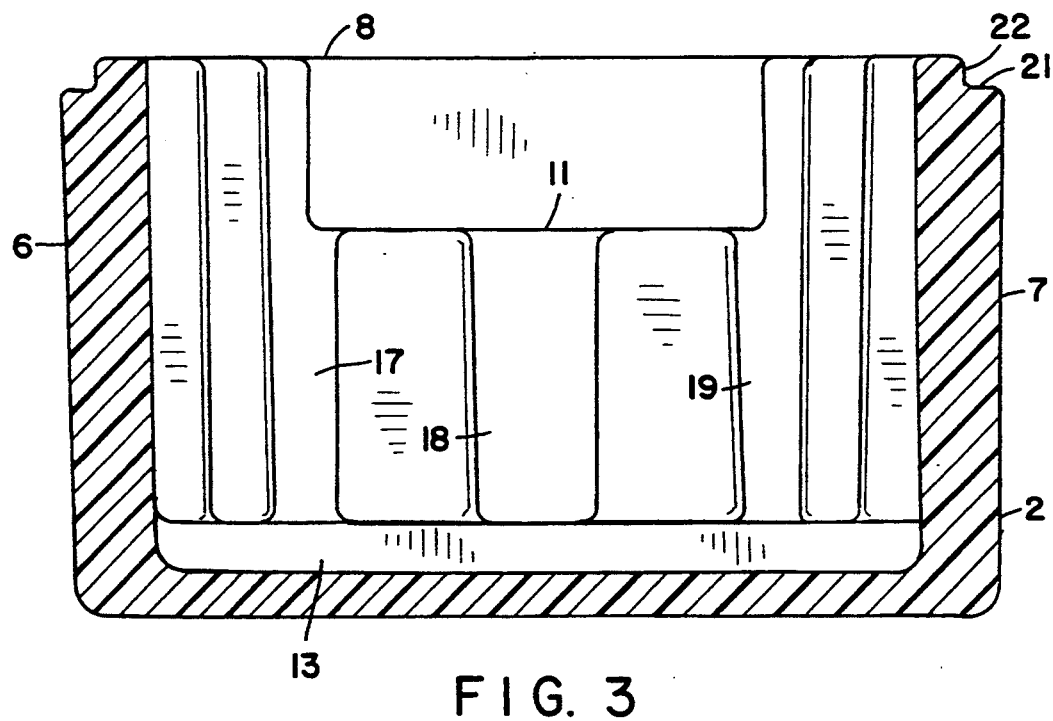
FIG. 3 is a cross-sectional view of the base along the line 3—3 shown in FIG. 2.
Figure 6:
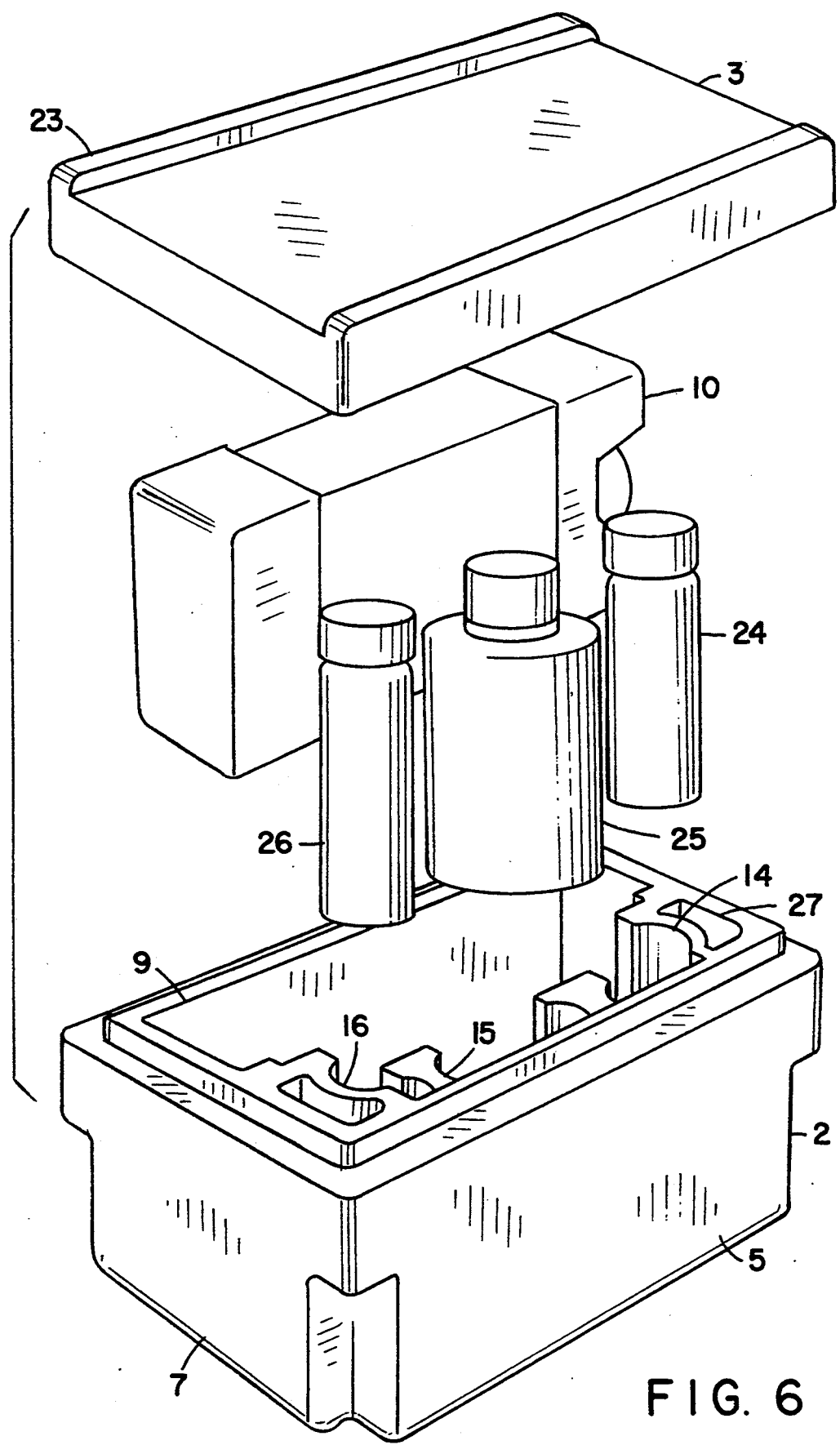
FIG. 6 is an exploded view of the container of the present invention and its contents.

Base 2, shown empty in FIGS. 2 and 3, includes a plurality of compartments and recesses therein. Base 2 has substantially parallel front 4 and rear 5 exterior walls and substantially parallel exterior side walls 6 and 7, and a top wall 8 through which the recesses and compartments lie. Base 2 includes a compartment 9, which extends longitudinally with respect to the base 2 and is rectangular in longitudinal cross-section, for receiving a temperature regulating means 10 (shown in FIGS. 4, 6 and 7), a recessed socket region 11 and a thermal expansion and passage space 12, which is also rectangular in longitudinal cross-section, between compartment 9 and region 11.

Figure 7:
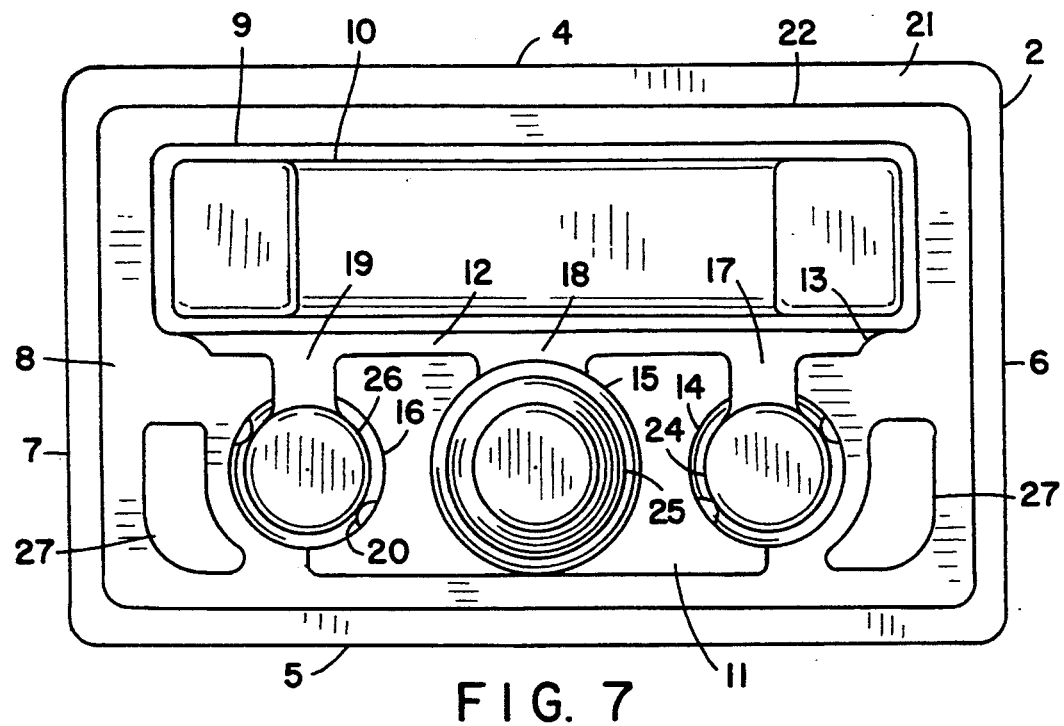
FIG. 7 is a top view as in FIG. 2 showing an ice pack in the rectangular compartment and specimen samples in the sockets.
Figure 4:
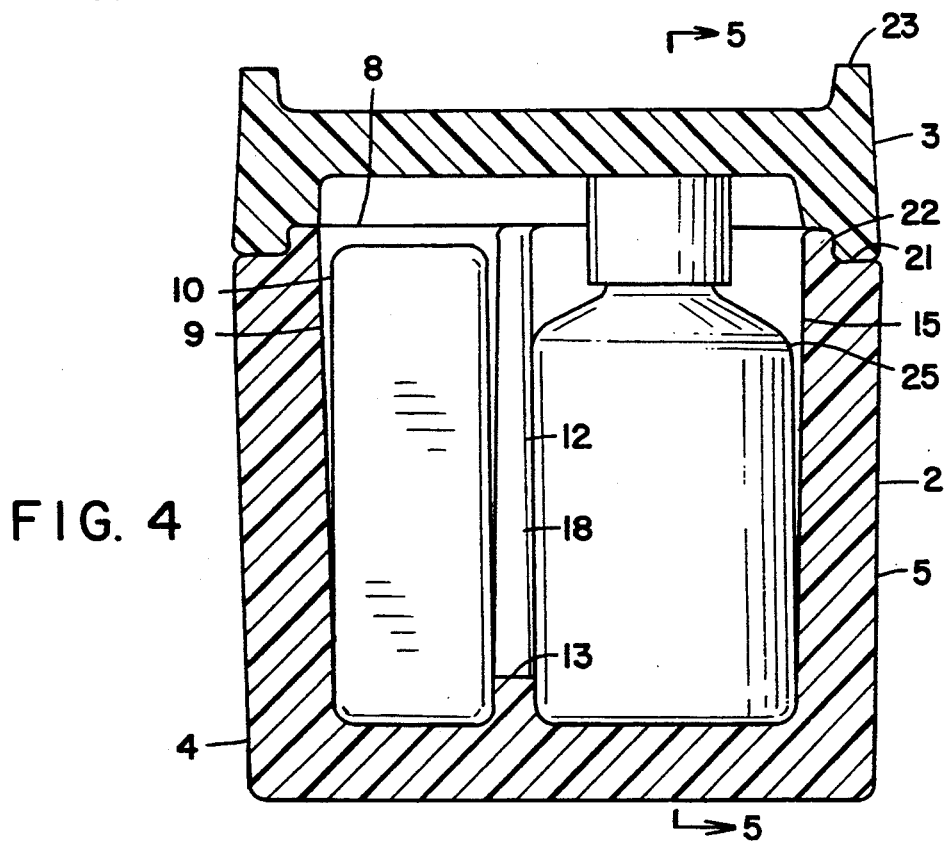
FIG. 4 is a cross-sectional view of the container along the line 4—4 in FIG. 1, showing a cold pack in the rectangular compartment and a specimen bottle in a socket.

Rectangular compartment 9 in base 2 receives and holds a rectangularly-shaped temperature regulating means 10, such as a cold or hot pack, which preferably forms a close fit within the compartment. Since the majority of biological and chemical samples require cooler temperatures to preserve the sample, the remainder of the description will be directed to the cold pack embodiment. It should be understood, however, that the invention is not limited to the cold pack embodiment. In both embodiments, however, the means 10 has a shape and size commensurate with that of the compartment 9 so that the cold or hot pack 10 forms a close fit therein, as shown in FIGS. 4 and 7.

Compartment 9 is separated from the recessed socket region 11 by a narrow strip 13, which serves to contain cold pack 10 within compartment 9, which forms the narrow expansion space 12. Since water and most cold pack materials expand upon freezing, cold pack 10 when frozen usually occupies more volume than when unfrozen. Since cold pack 10 when unfrozen preferably forms a close fit within compartment 9, attempts by consumers to force an expanded frozen cold pack 10 into a space the same size as compartment 9 could damage the container 1, undermining its insulating capacity as well as its structural integrity. Consequently, the present invention has provided the thermal expansion and passage space 12 contiguous with compartment 9 and into which the expanded cold pack 10 can extend if required. Preferably, cold pack 10 expands upon freezing primarily along the lateral side portions substantially parallel with front wall 4 and not along the other sides. In addition to receiving the expansive excess of cold pack 10, space 12 also serves to facilitate thermal communication between the cold pack 10 and the specimens.

Socket region 11, which extends longitudinally with respect to base 2 and is substantially parallel with rectangular compartment 9, includes a plurality of sockets 14–16 shaped to receive articles therein. Sockets 14–16 are preferably cylindrically-shaped to receive specimen bottles, test tubes or other like containers. Socket region 11 is preferably recessed from top wall 8 a sufficient amount to allow easy manual access to the exposed upper portions of the specimen containers therein. As shown in the figures, recessed socket region 11 need not extend longitudinally to walls 6 or 7 of base 2, but may terminate within end sockets 14 and 16. The space above socket region 11, shown in FIGS. 3 and 5 and being contiguous with both space 12 and compartment 9, is in thermal communication with cold pack 10, cooling the exposed upper portions of the specimen containers therein.

Figure 5:
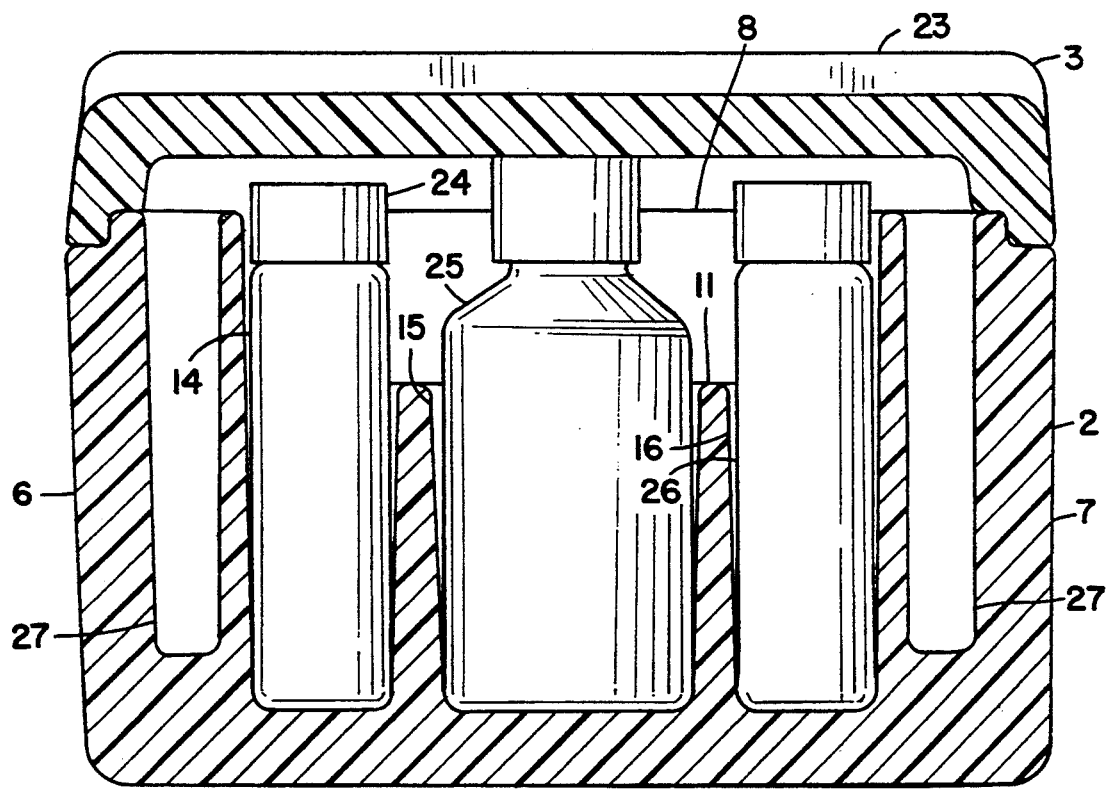
FIG. 5 is a cross-sectional view of the container along the line 5—5 in FIG. 4.

To enhance thermal communication, a plurality of channels 17–19 extend between the thermal passage space 12 and the sockets 14–16, respectively, facilitating thermal communication between the cold pack 10 and the enclosed specimens. As shown in the figures, the size and shape of the channel openings 17–19 varies with the size and shape of sockets 14–16. Although the channels 17–19 preferably extend along the longitudinal depth of each of sockets 14–16, as shown in FIGS. 3 and 5, it should be understood that alternative or partial openings which permit thermal circulation between the sockets 14–16 and cold pack 10 are within the scope of the present invention.

To further enhance thermal communication between the cold pack 10 and the specimens in sockets 14–16, each socket may include a plurality of ribs 20, shown in FIG. 2, extending vertically along the longitudinal depth of the socket. The ribs 20 maintain the enclosed specimens out of surface contact with their respective sockets, forming a narrow gap therebetween. Cooled air from cold pack 10 circulating within the space above the recessed socket region 11 may thus pass downward into the gaps and contact the specimen container sides, further facilitating thermal communication.

Alternatively, each specimen container may form a close friction fit within its respective socket. Further, the sockets 14–16 may be slightly undersized or tapered, as shown in FIGS. 4 and 5, to tightly receive and hold the specimen containers or other articles therein. In either embodiment, the enclosed specimen containers should fit snugly within its respective socket, and yet have a degree of yieldability, allowing easy removal of the specimen. Additionally, the ribs 20 may taper within the socket, and both the ribs 20 and sockets may taper together to form a tight fit for a specimen container. Tapering of the sockets 14–16 and compartment 9 not only allows tight engagement of the bottom portions of the specimen container 24–26 and cold pack 10, respectively, therein, but creates interstices along the sides of the upper portions thereof, further facilitating thermal communication.

As shown in the figures, the perimeter of top wall 8 of base 2 has a step configuration including a land portion 21 and riser portion 22 for engaging corresponding components of cover 3. Molded out of the same or similar insulating material as base 2, cover 3 may include ridges 23 along its longitudinal length for holding literature, mailing labels or other relatively flat articles. It should be understood that cover 3 has a configuration and thickness sufficient to overlie base 2 and form a tight seal thereon, thereby insulating the enclosed specimens.

Shown in FIGS. 4–7 is a test kit container 1 of the present invention, where base 2 contains a cold pack 10 within compartment 9 and specimen containers 24–26 within sockets 14–16, respectively. When not used, the cold pack 10 may be stored in compartment 9 in an unfrozen state. When removed and frozen, cold pack 14 may expand, preferably laterally, and upon reinsertion into compartment 9 the additional volume extends into expansion space 12. Specimen containers 24 and 26, shown within sockets 14 and 16, respectively, are not in surface contact with the socket sides because of the ribs 20, forming a gap allowing thermal communication with the side surfaces of the enclosed containers. Specimen container 25, although not in surface contact with the side of tapered socket 15 along the upper portion, forms a close friction fit with the side surface of the narrower socket 15 along the bottom.

Also shown in the figures are optional cavities 27 extending into top wall 8 substantially parallel to end sockets 15 and 17. An advantage of employing cavities 27 in the present invention is reduction in material usage and weight.

It should be understood that although the preferred shape of compartment 9 is rectangular and cold pack 10 is a rectangular parallelepiped of similar dimensions, alternative but commensurate configurations, such as a L-shaped compartment 9 and an L-shaped cold pack 10 should be considered within the scope of the present invention. Further, base 2 may include a plurality of compartments 9 for having a corresponding number of packs 10.

It should be understood that although the preferred shape of the sockets 14–16 and articles therein are cylindrical, alternative shapes are within the scope of the present invention. It should also be understood that cylindrical sockets 14–16, as shown in the figures, may differ in diameter. Further, the size and shape of the channel or opening along the longitudinal depth of a socket may vary. For example, the opening along socket 15 in the figures is larger than the openings along end sockets 14 and 16 because of the increased diameter of socket 15 and the need to facilitate thermal communication between the larger specimen container 25 within socket 15 with cold pack 10.

Although preferred embodiments of the present invention have been described and illustrated, it will be apparent to those skilled in the art that various modifications may be made without departing from the principles of the invention.

What is claimed is:

1. A container for transporting temperature sensitive materials therein, comprising:
   a base having a top surface;
   a compartment extending from the top surface into the base;
   a temperature regulating means housed in said compartment;
   a plurality of sockets extending from the top surface into the base, said plurality of sockets being adjacent with the compartment;
   an expansion and thermal passage space disposed between said compartment and said plurality of sockets;
   a channel extending between said expansion and thermal passage space and at least one of said plurality sockets; and
   a cover adapted to closely overlie the base along the top surface, said base and cover being formed from an insulating material.

2. The container of claim 1, wherein said temperature regulating means is selected from a group consisting of a cold pack, an ice pack and a hot pack.

3. The container of claim 1, wherein said plurality of sockets are substantially parallel with the compartment.

4. The container of claim 1, wherein at least one of said plurality of sockets is cylindrical.

5. The container of claim 1, wherein at least one of said plurality of sockets is tapered.

6. The container of claim 1, wherein said base is made from an insulating and yieldable material, and at least one of said plurality of sockets is slightly undersized for the intended article, whereby the article is held tightly within said socket.

7. The container of claim 1, wherein at least one of said plurality of sockets includes a plurality of ribs extending along the inner surface of said at least one socket.

8. The container of claim 7, wherein said plurality of sockets extends substantially perpendicularly from the top surface into the base and said plurality of ribs extend substantially longitudinally along the inner surface of the sockets.

9. The container of claim 1, wherein said insulating material is selected from the group consisting of styrofoam, polystyrene and expanded polystyrene.

10. The container of claim 1, wherein the sockets extend into said base along a surface recessed from and substantially parallel with the top surface.

11. A test kit container for transporting temperature sensitive materials therein, comprising:
    a base having a top surface;
    a temperature regulating means;
    a compartment extending substantially perpendicularly from the top surface into the base and housing the temperature regulating means therein;
    a plurality of cylindrical sockets extending substantially perpendicularly from the top surface into the base, said plurality of cylindrical sockets being adjacent with the compartment;
    an expansion and thermal passage space disposed between said compartment and said plurality of sockets;
    a channel extending between said expansion and thermal passage space and at least one of said plurality of cylindrical sockets; and
    a cover adapted to closely overlie the base along the top surface, said base and cover being formed from an insulating material.

12. The container of claim 11, wherein said temperature regulating means is selected from the group consisting of a cold pack, an ice pack and a hot pack.

13. The container of claim 11, wherein at least one of said plurality of sockets is tapered.

14. The container of claim 11, wherein a plurality of ribs extends substantially longitudinally along the inner surface of said at least one socket.

15. The container of claim 11, wherein said plurality of sockets are substantially parallel with the compartment.

16. The container of claim 11, wherein said insulating material is selected from the group consisting of styrofoam, polystyrene and expanded polystyrene.

17. The container of claim 11, wherein the sockets extend into said base along a surface recessed from and substantially parallel with the top surface.

* * * * *